United States Patent [19]

Abrahams

[11] 3,963,685

[45] June 15, 1976

[54] ALCOHOL SOLUBLE HYDROPHILIC POLYMER VIA AQUEOUS POLYMERIZATION

[76] Inventor: Robert A. Abrahams, 12 Amherst Road, Malboro, N.J. 07746

[22] Filed: May 13, 1974

[21] Appl. No.: 469,161

[52] U.S. Cl............................ 526/230; 128/155; 128/156; 204/159.22; 260/29.6 R; 260/29.6 T; 260/30.2; 260/30.8 DS; 260/32.6 R; 260/33.2 R; 260/33.4 R; 260/33.8 UA; 424/78; 424/81; 526/317; 526/320; 526/323; 526/325; 526/329
[51] Int. Cl.²................ C08F 216/04; C08F 220/20
[58] Field of Search......... 260/86.1 E, 80.73, 80.75; 204/159.22

[56] References Cited
UNITED STATES PATENTS

| | | | |
|---|---|---|---|
| 3,575,946 | 4/1971 | Chromecek et al............ | 260/86.1 E |
| 3,607,848 | 9/1971 | Chromecek et al............ | 260/86.1 E |
| 3,671,502 | 6/1972 | Samour et al.................. | 260/80.73 |
| 3,699,089 | 10/1972 | Wichterle..................... | 260/86.1 E |

*Primary Examiner*—Harry Wong, Jr.
*Attorney, Agent, or Firm*—Cushman, Darby & Cushman

[57] ABSTRACT

Hydrophilic, water insoluble, organic solvent soluble polymers of hydroxyalkyl methacrylate or acrylate of high purity are prepared in water using hydroxyalkyl methacrylate or acrylate monomer having not over 0.035 weight percent of alkylene glycol dimethacrylate or diacrylate. The polymers have high molecular weight and narrow molecular weight distribution and are useful for medical applications, e.g., as a burn dressing.

16 Claims, 1 Drawing Figure

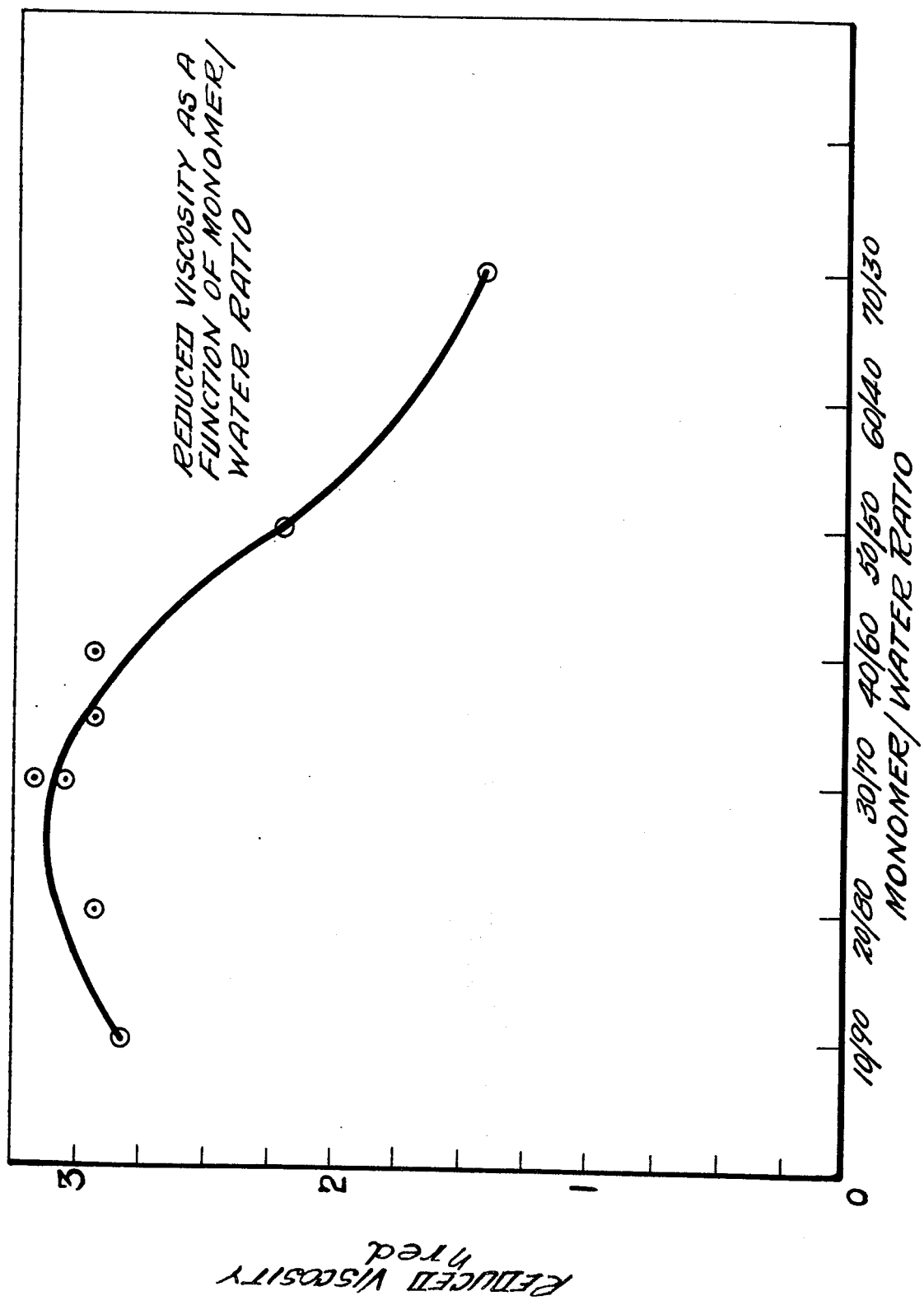

ALCOHOL SOLUBLE HYDROPHILIC POLYMER VIA AQUEOUS POLYMERIZATION

It has previously been proposed to make organic solvent soluble, water insoluble polymers of hydroxyalkyl methacrylate or acrylate, e.g., of 2-hydroxyethyl methacrylate. Such hydrophilic polymers are capable of generating a water insoluble hydrogel and are also soluble in many organic solvents, e.g., mono- and polyalcohols such as methyl alcohol, ethyl alcohol, propyl alcohol, isopropyl alcohol, ethylene glycol, propylene glycol, diethylene glycol, triethylene glycol, and higher polyethylene glycols having molecular weights upwards to several hundred. They also can be soluble in alcohol mixtures, e.g., 95% alcohol, but are not soluble in water alone.

They have been prepared by suspension polymerization, e.g., Shepherd U.S. Pat. No. 3,618,213. Such a procedure involves the use of toxic organic materials which at considerable expense, must be removed for medical and certain other uses. They have also been prepared in the presence of certain organic solvents, Chromacek U.S. Pat. No. 3,575,946.

However, when hydroxy lower alkyl methacrylates or acrylates, e.g., 2-hydroxyethyl methacrylate, have been polymerized in water, i.e., starting out as an aqueous solution the product has invariably been a cross-linked, organic solvent insoluble product. Typical examples of making such cross-linked polymers are shown in Wichterle U.S. Pat. No. 2,976,576 and Wichterle U.S. Pat. No. 3,220,960.

Even using organic solvents during polymerization, the hydrophilic product is frequently cross-linked and organic solvent insoluble, e.g., Wichterle U.S. Pat. No. 3,699,089.

It has now been found that hydrophilic, water insoluble, organic solvent soluble, e.g., lower alkanol soluble, polymers can be prepared by polymerizing in water a hydroxy-lower alkyl methacrylate or acrylate. monomer of the formula

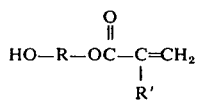

wherein R is an alkylene group of 2–3 carbon atoms, e.g., ethylene or propylene and wherein R' is hydrogen or methyl, providing the amount of diester is not over 0.035 weight percent, based on the weight of monomer, said diester having the formula

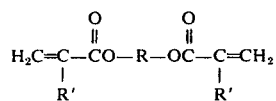

wherein R and R' have the meanings noted above. The resulting hydrophilic polymer, while being insoluble in water, is soluble and hence capable of forming a solution in organic solvents such as those set forth above, e.g., mono- and polyalcohols such as methyl alcohol, ethyl alcohol, isopropyl alcohol, propyl alcohol, ethylene glycol, propylene glycol, the polyalkylene glycols, such as the polyethylene glycols including diethylene glycol, triethylene glycol and higher polyethylene glycols of molecular weights up to 800, and higher. They also are soluble in alcoholwater mixtures containing a predominant amount of alcohol, e.g., 95 weight percent alcohol.

The polymers of the present invention as stated are soluble in alcohol, e.g., ethyl alcohol. They can be prepared in a system combining a given quantity of monomer, charged with initiator (or the initiator can be omitted as explained hereinafter) and with a given quantity of water. For medical applications, it is preferable to use sterile and pyrogen free water (although the polymeric product of course can be sterilized).

Alcohol soluble products have been obtained at monomer to water ratios ranging from 10:90 through 70:30. The preferred ratio of monomer to water is 35:65 because this yields a homogeneous spongy mass which is particularly amenable to further treatment, e.g., grinding and/or purification. Its porous nature makes purification, e.g., removal of unreacted monomer, a simple leach process. The 35% monomer lever is far above the levels permissible by previous methods.

Conversion rates of monomer to polymer of over 99.5% have been obtained with recoveries over 99%.

The polymerization temperature is not critical. Thus, temperatures from about 20°C. to the boiling point of water can be used. However, it has been found preferable to heat the mixture, most preferably to 65°C. This can be attained for example: (1) in an oven; (2) in a water bath; (3) pre-heating of the water in the reaction vessel with subsequent introduction of the monomer.

Polymerization time, of course, is temperature dependent. At 65°C. the time is usually 20–40 minutes.

If it is desired to subsequently cross-link the linear polymer produced by the invention this can be accomplished by conventional procedure, e.g., addition of alkali metal dichromate, e.g., sodium or potassium dichromate or ammonium dichromate in an amount of 0.05 to 2.5%, usually less than 1%, e.g., 0.2% of ammonium dichromate based on the amount of polymer.

Comonomers can be added as long as they are water miscible.

The soluble products of the invention have relatively high reduced viscosities which are indicative of high molecular weights. Thus, they can be prepared with average molecular weights above about 50,000, generally above about 250,000, and usually above 1,000,000. The molecular weight can be preselected and controlled by appropriate charge of initiator.

The polymeric product, moreover, has a narrow range of molecular weights which makes its properties more homogeneous than those prepared by prior techniques.

The removal of all residuals, including unreacted monomer is readily effected to below 1 ppm by a series of successive washes with water, for example, 5–7 successive washes with sterile water using a water to polymer ratio of 4:1.

The use of a chemical initiator can be obviated, thus removing another source of impurities, by utilizing irradiation, e.g., $Co^{60}$ gamma irradiation, ultraviolet light as the polymerization initiator.

When a free radical catalyst is used, it is generally employed in an amount of 0.05 to 1%, usually 0.1 to 0.4% of the monomer. Typical catalysts include t-butyl peroctoate, benzoyl peroxide, isopropyl percarbonate, methyl ethyl ketone peroxide, cumene hydroperoxide, dicumyl peroxide, potassium persulfate, azo-bisisobutyronitrile, t-butyl hydroperoxide, di-t-butyl peroxide, p- cumene hydroperoxide.

Unless otherwise indicated, all parts and percentages are by weight.

The polymers of the present invention can be used wherever water insoluble hydrophilic polymers of hydroxyalkyl methacrylate or acrylate are employed. Thus, they can be used for any one of the uses disclosed in Chromacek U.S. Pat. No. 3,575,946; Shepherd U.S. Pat. No. 3,618,213; Wichterle U.S. Pat. No. 2,976,576; Wichterle U.S. Pat. No. 3,220,960; Shepherd U.S. Pat. No. 3,567,118; Shepherd U.S. Pat. No. 3,574,822; Shepherd U.S. Pat. No. 3,577,512; Shepherd U.S. Pat. No. 3,557,518; Gould U.S. Pat. No. 3,641,237; Gould U.S. Pat. No. 3,577,516. The entire disclosures of all of the patents mentioned in this paragraph are hereby incorporated by reference.

For example, medicinally active ingredients such as germicides, fungicides, antibiotics, analgesics, or the like may be utilized by having the medicinally active ingredient suspended, encapsulated or entrapped in the polymer or if desired dissolved in the liquid phase of the system. Examples of such medicinally active ingredients include silver sulfadiazine, benzocaine, xylocaine, aspirin, sodium omadine (a derivative of 1-hydroxypyridine-2-thione), hexachlorophene, bacitracin, cortisone, trimethyl benzyl ammonium chloride, cetyl pyridinium chloride, penicillin, Aureomycin (chlorotetracycline), chloromycetin (chloromphenicol), merthiolate, sulfanilamide, sulfathiazole, sulfaguanidine, sulfapyridine, salicyclic acid, Griseofulvin, undecylenic acid, zinc undecylenate, tetracycline, hydroxytetracycline (Terramycin), silver nitrate, ascorbic acid.

The polymer can be micropulverized to particles of a dimension smaller than 50 mesh, preferably below 150 mesh (Tyler sieve) for some uses, e.g., in burn bandages. Bulk density of the hydrophilic, water insoluble, organic solvent soluble polymer, especially polymers of 2-hydroxyethyl methacrylate, is normally higher than 0.60 g/cc for powder in the 100 to 375 mesh range. Thus, the polymer at a mesh size of 220 had a bulk density of 0.8 and was non-tacky.

The hydroxyalkyl methacrylate and acrylate polymers prepared by aqueous bulk polymerization using ultra-pure monomers characterized by a very low concentration of impurities conducive to cross-linking reactions of the present invention which can be prepared under "clean conditions" easily purified from residual monomers, and easily reduced to powders of the desired particle size are particularly useful in preparing burn bandages as described in Ronel application entitled Burn Bandages, filed on even data herewith.

Medically active ingredients can be incorporated into the burn dressing using the polymers of the present invention by one of more of the following procedures.

A. Incorporation in the hydrophilic powder by any of the processes described in Gould U.S. Pat. No. 3,576,760, the entire disclosure of which is hereby incorporated by reference.

B. Incorporation in the liquid phase by mixing the solubilizing agent with the drug. The drug does not have to be soluble in the liquid.

The polymers of the invention can be used as indicated in said Ronel application to treat burns, e.g., third and fourth degree burns on any skin surface, e.g., on the arms, legs, face, back, head or stomach. The invention is useful not only in treating humans, but also in veterinary medicine, e.g., to treat burns on dogs, cats, sheep, cattle, rabbits, guinea pigs, horses and zoological animals such as lions, tigers, deer, zebra, etc.

The synthetic film of hydrophilic polymer forms on the open surface of the burn and molds itself to the granulating wound.

EXAMPLE 1: PREPARATION OF A HYDROGEL FOR BURN DRESSING:

Hydroxyethyl methacrylate of the following purity: HEMA- min. 99.4%, Ethyleneglycol dimethacrylate — less than 0.035%, other impurities — less than 0.5 %, was passed through a micronite filter (Micropore — less than 1 micrometer pore size). The monomer (1,000 g) was mixed with pyrogene-free, deionized (conductivity: 2 mg ohm) water (2,330 g). After addition of isopropyl peroxidicarbonate (3 g), the mixture was placed in a polyethylene container, degassed by bubbling nitrogen gas for 10 minutes, and placed in a 65°C. oven for 30 minutes. The resulting hydrogel was placed in water of the same purity as above during several days. Water was changed daily until no extractable could be detected in the leach water. The polymer was then oven dried at 40°C., ground and micropulverized to −200 mesh in a stainless steel micropulverizer. The bulk density of the resulting powder was 0.73 g/cc. The intrinsic viscosity in methyl Cellosolve (methoxyethanol) was 1.6 dl/g indicating a molecular weight above 1,000,000. The rate of dissolution was followed by measuring the increase of Brookfield viscosity of a solution of 10% polymer in 800 g Carbowax 400 (polyethylene oxide molecular weight 400) (Spindle No. 2) as a function of time for the fraction between −200 and −375 mesh. During the first hour, the viscosity increase rate, which reflects the rate of dissolution of the particles, was less than 2 poise/hour compared to more than 5 poise/hour for conventional HYDRON-S of similar intrinsic viscosity. (Hydron-S is a commercially available solvent soluble essentially homopolymeric hydroxyethyl methacrylate).

All the operation was carried out under clean conditions in a room equipped with laminar flow hoods, adequate air filters. The powder was packaged in glass vials equipped with a cap pierced with 1mm holes (i.e., salt shaker) and sealed with a pressure adhesive label. The vials were sterilized by irradiation and checked for sterility.

Polyethylene glycol molecular weight 400 (USP) was placed in a 100 ml serum vial, stoppered, sterilized by autoclaving.

A 2 square inch third degree burn on the back of a rabbit was covered with an occlusive dressing within the 20 minutes following the trauma, in the following way: Polyethylene glycol 400 (USP) was withdrawn from the serum vial with a 5 cc sterile hypodermic needle and deposited on the wound. The needle was used to spread the liquid evenly. The hydrogel powder was then applied on the layer of polyethylene glycol 400 by slowly shaking the powder vial.

MATERIALS: All of the polymers within the invention produced below except in Table 5 were made using a single batch of distilled HEMA (hydroxyethyl methacrylate), the analysis of which is given in Table No. 1.

TABLE NO. 1

Analysis of HEMA Monomer

| | |
|---|---|
| DEGMA (diethylene glycol methacrylate) | 0.04% |
| EGDMA (ethylene glycol dimethacrylate) | 0.02% |
| MAA (methylacrylic acid) | 0.11% |
| LOWER BOILERS | 0.48% |
| HIGH BOILERS | <0.05% |
| MEHQ (methyl ether of hydroquinone) | 73 ppm |
| TOTAL IMPURITIES | (not over 0.77%) |

For the purpose of comparison, samples of suspension grade (HEMA Type N (Polymer X) and solution HEMA Type N (Polymer Y) polymers were obtained.

Polymerization Procedure

The polymers which constitute the basis of the present invention were produced from an unadjustable portion of monomer whose initiator — isopropyl percarbonate (IPP) — concentration was brought to a level of 0.3%. Quantities of this monomer were then weighed out and placed in 21×11cm Nasco Whirl-Pak polyethylene bags along with the appropriate quantity of Travenol nonpyrogenic sterile water so as to bring the total weight to 100 grams. The following monomer/water ratios were prepared: 10/90, 20/80, 25/75, 30/70, 35/65, 40/60, 50/50, 70/30. The 30/70 test was run in duplicate in order to estimate reproducibility.

Each of the aqueous solutions of monomer was bubbled through with nitrogen gas for 1 minute to ensure that a minimun of oxygen, which can inhibit polymerization, is present. The polyethylene bags were then individually placed in metal frame retainers which limited their thickness to approximately 1 cm. This was done to ensure a minimal thermal gradient during heating and to give products of comparable dimensions. The bags were then placed in a water bath maintained at 65°C. for a period of 40 minutes.

Upon removal from the bath each bag was allowed to cool for an hour, after which a small piece from the center of the material was removed in order to perform a methanol solubility test.

Solubility Test

Solubility tests consist of placing about 0.1 grams of polymer into 2.0 grams of methanol. If complete dissolution is not observed within 30 minutes, the sample is left on a roller overnight. Each of the polymers formed was tested both upon formation and after purification and drying. Furthermore, the polymer produced using a 35/65 ratio, having been found to yield the most uniform product, was tested for solubility in a series of organic solvents.

Purification

The remainder of the polymer was cut up and placed in a blender along with sufficient deionized water to give a total water content equal to ten times the initial monomer weight. Grinding in the blender was carried out for about 3 minutes, or until the particles averaged about 2–4 mm in size. The liquid was then decanted and replaced by an equivalent quantity of fresh deionized water. Agitation in the blender was continued at low speed for another 5 minutes after which the liquid was decanted. These supernates were identified as WASH No. 1 and WASH No. 2. The polymer was placed in a clean jar with a volume of fresh deionized water equal to that recovered from WASH No. 2 and set aside to leach. The leach water was changed three additional times at intervals ranging from 8 to 72 hours. Aliquots of the leach waters were analyzed in the UV spectrophotometer for free monomer content and selected samples were submitted for gas chromatographic analysis which, heretofore, has been deemed more accurate than UV spectrometry.

Between leaches the polymers were squeezed between glass plates to remove occluded water and were then blotted with Whatman Grade 1 filter paper. Above a 30/70 monomer/water ratio it was not possible to extract any liquid on squeezing. The liquid obtained from all lower ratios was retained in order to ascertain whether or not the entrapped liquid had the same HEMA concentration as the free liquid, i.e., whether or not a HEMA equilibrium is established between the liquids.

After the final leaching the polymers were placed in a vacuum oven maintained at 38°C. to dry to constant weight. The dried polymers were placed in the blender and were ground to a granular powder after which they were returned to the oven overnight. A weighing of the dried product gave an estimate of material recovery whereas the free monomer content of the wash and leach waters gave an estimate of monomer conversion. The products were stored in a vacuum desiccator prior to further testing.

Diester and Initiator Concentrations

It was determined quite early in this work that the alcohol solubility of the polymers produced in aqueous solution was governed rather critically by the EDGMA concentration. The effect that altering the initiator concentration had on polymers with varying diester concentrations was included in this study.

Cross-Linkability

The cross-linkability of the organic solvent soluble polymer made from 35/65 HEMA/water was tested by adding 0.2 phr of ammonium dichromate to a methanol solution of the polymer and casting a film. The film was cured in a room lit by fluorescent light. A control film containing no dichromate was prepared at the same time. The solubility of the films was then tested in methanol.

Post-Cure

A test was performed to determine whether or not an extended cure time produced a cross-linked product. A 35/65 test solution was placed in the 65°C. bath for 5 hours and its solubility was determined.

Copolymers

It was also determined that soluble copolymers could be similarly produced in aqueous solution. To this end, three copolymers were prepared. They were all 35/65 monomer to water, with the monomeric components having the following compositions:

$H_{90}/MAA_{10}$ — 10% methacrylic acid, 90% HEMA $H_{90}/Q1_{10}$ — 10% Sipomer Q1 (a water soluble quaternary methacrylate, $CH_2=C(CH_3)COOCH_2CH(OH)CH_2N(CH_3)_3Cl$) 90% HEMA $H_{40}/EeA_{48}/H_pA_{12}$ — 48% ethoxyethylacrylate, 12% hydroxypropylacrylate, 40% HEMA.

The IPP content for each of these copolymers was about 0.3%.

Physical Properties

On each of the polymers there was determined the reduced viscosity, $n_{red}$. Also, as part of the comparison with poly (HEMA) formed by other techniques samples of the 35/65 polymer were submitted, along with Polymer X and Polymer Y for intrinsic viscosity measurements. A film of each of these was cast from methanolic solution and submitted for infrared analysis. Purified polymers which were reprecipitated from methanol were used for a nuclear magnetic resonance structure analysis.

DISCUSSION OF RESULTS WITH POLYMERS PREPARED ACCORDING TO THE INVENTION

Qualitative Evaluation

The following observations were recorded on the effect of the monomer/water ratio:

10/90: A white suspension which agglomerates into a unified mass on shaking. This mass was very porous, and spongy. About 75 ml of free liquid was obtained. On grinding and standing in leach water the particles re-agglomerate to form a mass which did not break upon shaking.

20/80: Two distinct polymeric layers. The top two-thirds was identical in appearance to the 10/90 material while the lower part was a white but less porous and less elastic polymer. There were about 52 ml of excess liquid present. On grinding, this material also agglomerated to itself. Note: both layers were combined in the blender.

25/75: As with 20/80, two distinct polymeric layers were formed but only the top one-third was the elastic material of type 10/90. About 24 ml of excess liquid was recovered. After grinding the particles were found to break apart quite easily on shaking.

30/70: The product was white and spongy but not nearly as elastic as 10/90. There was a small quantity (~0.5 ml) of excess liquid present.

30'/70: The product appeared to be identical to the previous polymer. There was about 2.5 ml of excess liquid present.

35/65: The product was white and spongy. There was no excess liquid present nor was any phase separation noted.

40/60: This material was as white as 30/70 and had no excess liquid present. However, there was a small amount of phase separation detected. This second phase was a clear, tacky gel which was most prominent at the top surface. It is likely due to the presence of an excess of monomer in the initial solution. This polymer is more rubbery than spongy.

50/50: The product was less white than 40/60 and much more rubbery. There is also a greater quantity of the second, clear phase present.

70/30: This product was a clear gel with some bubble entrapment. There is no excess liquid present and, in fact, the polymer feels dry to the touch. It was extremely rubbery and could not be ground in the blender until after it turned brittle on drying. In the leach water the particles, which were obtained by cutting the polymer with scissors, were found to adhere to one another.

In general, all of the solutions, except 70/30, in the above series were found to turn opaque after about 5–7 minutes. All of the "CRUDE" polymers, regardless of the monomer/water ratio, were found to be methanol soluble.

Effect of High Inhibitor Content

During this series of experiments, a group of polymers was prepared from a monomer which had a moderately high inhibitor concentration. The resultant polymers were found to be off-white in color, more rubbery than spongy with a greater amount of phase separation than obtained when using a purer grade of monomer.

Polymeric Purification

As noted earlier, each polymer in the series 10/90 to 70/30 was washed twice in a blender for from 3 to 5 minutes. Each was then leached four times, the duration of these leaches being:

| LEACH No. 1 | = | 18 hours |
|---|---|---|
| LEACH No. 2 | = | 72 hours |
| LEACH No. 3 | = | 8 hours |
| LEACH No. 4 | = | 18 hours |

A UV-analysis was performed on carefully diluted leach waters. HEMA exhibits a characteristic peak at about 208 m$\mu$.

The wash waters for each sample were submitted for gas chromatographic analysis, along with some of the leach waters. The results obtained from all analyses are to be found in Table No. 2. In this table the values contained in parentheses are those obtained on the gas chromatograph. It can be seen that quite favorable agreement exists between the results obtained by the two methods. The two values contained in brackets were obtained from repeat G.C. analyses, as a test of reproducibility.

An apparent discrepancy between WASH No. 2 and LEACH No. 1 for the 50/50 and 70/30 polymers is explained by the fact that these materials are less porous than the other samples and require more time to elute the entrapped monomer.

Analysis of the excess liquid present following the 30'/70 reaction indicated this liquid to contain 5.4% monomer, which, in 2.5 ml, represents 0.13 grams. This is equivalent to 0.4% of the initial weight of monomer.

It is worthwhile to compare the percentages of the total quantity of leached monomer that are contained in each of the washes and leaches. This information is contained in Table No. 3. It is apparent from this table that those materials which contained excess liquid and a very porous phase contain over seventy percent of the unreacted monomer in the first wash, whereas those materials which exhibited phase separation and were more rubbery and less porous contained less than fifty percent. Those products with the desireable combination of little unreacted liquid and no phase separation yielded just over fifty percent of the unreacted monomer during the first 3 minute wash in the blender.

TABLE No. 2

EFFICIENCY OF WASHING AND LEACHING AS DETERMINED BY GAS CHROMATOGRAPHY
AND ULTRA-VIOLET SPECTROPHOTOMETRY
PERCENTAGE OF UNREACTED MONOMER PRESENT IN SUPERNATES

| Sample | WASH No. 1 | WASH No. 2 | LEACH No. 1 | LEACH No. 2 | LEACH No. 3 | LEACH No. 4 |
|---|---|---|---|---|---|---|
| 10/90 | (5.340) | (1.270) | 0.1009 | 0.0179 | 0.0081 | 0.0039 (0.0030) |
| 20/80 | (2.570) | (0.530) | 0.0949 | 0.0192 | 0.0023 | 0.0008 (0.0008) |
| 25/75 | (1.366) | (0.389) | 0.1626 | 0.0577 | 0.0189 | 0.0049 (0.0068) |
| 30/70 | (0.335) | (0.174) | 0.0994 | 0.0307 | 0.0093 | 0.0037 (0.0035) |
| 30'/70 | (0.180) | (0.104) | 0.0774 (0.0795) | 0.0262 (0.0261) | 0.0080 (0.0088) | 0.0034 (0.0035) |
| 35/65 | (0.177)[0.172] | (0.090)[0.089] | 0.0560 (0.0585) | 0.0166 (0.0191) | 0.0041 (0.0053) | 0.0018 (0.0013) |
| 40/60 | (0.135) | (0.085) | 0.0574 | 0.0181 | 0.0038 | 0.0016 (0.0015) |
| 50/50 | (0.051) | (0.020) | 0.0250 | 0.0099 | 0.0026 | 0.0006 (0.0005) |
| 70/30 | (0.052) | (0.017) | 0.0260 | 0.0114 | 0.0024 | 0.0014 (0.0011) |

TABLE No. 3

PERCENTAGE OF TOTAL LEACHED UNREACTED MONOMER CONTAINED IN EACH EXTRACTION

| Monomer/Water | WASH No. 1 | WASH No. 2 | LEACH No. 1 | LEACH No. 2 | LEACH NO. 3 | LEACH No. 4 |
|---|---|---|---|---|---|---|
| 10/90 | 79.3 | 18.9 | 1.4 | .25 | .11 | .05 |
| 20/80 | 75.4 | 20.2 | 3.5 | .70 | .08 | .03 |
| 25/75 | 71.3 | 20.3 | 5.7 | 1.97 | .61 | .15 |
| 30/70 | 51.8 | 26.9 | 15.0 | 4.52 | 1.34 | .49 |
| 30'/70 | 53.9* | 22.0 | 16.4 | 5.42 | 1.61 | .65 |
| 35/65 | 51.5 | 26.2 | 16.0 | 4.65 | 1.13 | .49 |
| 40/60 | 45.8 | 28.0 | 18.6 | 5.86 | 1.25 | .52 |
| 50/50 | 47.7 | 18.5 | 22.3 | 8.71 | 2.29 | .51 |
| 70/30 | 48.2 | 15.4 | 23.3 | 9.86 | 2.09 | 1.22 |

*includes material contained in the 2.5 ml of excess liquid at the end of the reaction It was found that each of the leached polymers was alcohol soluble both before and after vacuum oven drying. Note must be taken of the fact that vacuum-oven dried polymer does not dry if in clumps. Although the outer material becomes dry, hard, brittle and transparent the polymer in the interior of the clump remains wet, soft, spongy and white. This necessitates further breaking up of clumps during drying and ultimately, to ensure thorough drying, dry grinding in a blender.

CONVERSION AND RECOVERY

Using the unreacted monomer concentration and the volume of each of the wash and leach waters one may use this information to estimate the extent of conversion of monomer to polymer for any given reaction. A sample calculation is contained in Table A. The percentage of conversion obtained for each of the polymers formed can be found in Table No. 4.

TABLE No. 4

CONVERSION RATE AND RECOVERY RATE OF POLY(HEMA)

| Monomer/Water | % Conversion | % Recovery |
|---|---|---|
| 10/90 | 52.8 | 31.7 |
| 20/80 | 74.4 | 65.1 |
| 25/75 | 85.8 | * |
| 30/70 | 95.4 | 85.0 |
| 30'/70 | 96.8 | 89.6 |
| 35/65 | 97.3 | 87.1 |
| 40/60 | 97.6 | 88.2 |
| 50/50 | 99.1 | 89.7 |
| 70/30 | 99.1 | * |

*Loss of these products in a mishap precluded the possibility of obtaining quantitative recovery data.

The weight of the final ground and dried product was a mesure of the percentage of material recovery. This information is included in Table No. 4.

It was obvious that material losses during grinding and other mechanical handling were disproportionately large when the polymers were prepared on such a small scale. As the scale of production is increased, these losses diminish and greater percentages of recovery are obtained.

Reduced Viscosity

Each of the purified and dried polymers of the series 10/90–70/30 were submitted for reduced viscosity measurements (i.e., 0.5% solution of polymer in methyl Cellosolve (monomethyl ether of ethylene glycol)). The values obtained are plotted in the Figure. This graph indicates the effect that the monomer/water ratio exerts on the viscosity, and, therefore, the molecular weight of the various species. A difference of 3.8% between the 30/70 and 30'/70 polymers is an indication of the reproducibility of different runs.

Two runs were performed at 0.2 and 0.1% diester (EDGMA) levels and gave insoluble products. One sample, run as 100/0 (HEMA/water) i.e., no water present, was insoluble in methanol indicating that the presence of water deters cross-linking.

Based upon the favorable appearance and ease with which they could be purified further work was restricted primarily to aqueous solutions containing 30–35% monomer.

Effect of Diester and Initiator Concentrations on Solubility

Table No. 5 summarizes the various conditions of diester and initiator concentrations that were employed in preparing samples of polymer. Their solubility in methanol is included in this table. It is evident from this table that the presence of methacrylic acid, in moderate proportion does not affect the solubility of poly(-HEMA). On the other hand, the presence of diester (EGDMA) has a marked effect on the solubility, and likely on most other properties, of the polymer. The effect of the cross-linking diester is influenced to a small degree, by the concentration of the initiator. However, it is quite probable that the soluble polymers produced by using an excess of IPP when the monomer is above the apparent critical EGDMA concentration of 0.035% have quite different structures from those prepared with diester below this level. As the diester concentration increases, the linearity which characterizes pure poly(HEMA) is gradually replaced by a highly branched polymer. The use of excess IPP has the effect of shortening the chain length thus compensating somewhat for the reticulation of the molecule by the EGDMA, and generates a soluble polymer.

Specific soluble polymers were submitted for reduced viscosity measurements in order to further characterize these materials as affected by diester and initiator. The results are included in Table No. 5. Comparing the results of Table No. 5 with the reduced viscosities of the Figure, indicates that viscosities are affected just as markedly by the diester concentration as was the solubility. Comparing either 30/70 or 35/65 samples which differ only in acid content indicates that methacrylic acid does not have a measurable effect on the viscosity at the moderate levels employed.

amount of EGDMA is not over 0.025% of the HEMA monomer.

PROPERTIES OF THE POLYMER

Having determined that polymers having an initial monomer/water ratio of 35/65 were the most homogeneous and having encountered no difficulty in purifying and handling this material this polymer was selected for further characterization.

Solubility

Table No. 6 contains the results obtained when polyHEMA made from 35/65 HEMA/water was added to a variety of solvents. It can be seen that solubility is limited to polar and hydroxylic solvents. This list is far from exhaustive but does indicate that co-solvent systems can affect the solubility of this material.

TABLE No. 5

EFFECT OF DIESTER AND INITIATOR CONCENTRATIONS ON POLYMER SOLUBILITY AND REDUCED VISCOSITIES

| Sample No. | Monomer/Water | MAA % of Total Monomer | EGDMA % of Total Monomer | IPP % of Total Monomer | Sol'y in MeOH | $n_{red}$ | Remarks |
|---|---|---|---|---|---|---|---|
| 1  | 10/90 | 0.31 | 0.04   | 0.00 | —    |       | no reaction after 5 hours |
| 2  | 30/70 | 0.07 | 0.02   | 0.99 | s    |       |  |
| 3  | 30/70 | 0.20 | 0.035  | 0.83 | s    |       |  |
| 4  | 30/70 | 0.30 | 0.05   | 0.30 | i    |       | All polymers in this |
| 5  | 30/70 | 0.30 | 0.05   | 0.40 | i    |       | series swell in methanol |
| 6  | 30/70 | 0.30 | 0.05   | 0.50 | i    |       | the extent of volume |
| 7  | 30/70 | 0.30 | 0.05   | 0.60 | i    |       | expansion increasing as |
| 8  | 30/70 | 0.30 | 0.05   | 0.71 | sl.s.|       | the initiator concentra- |
| 9  | 30/70 | 0.30 | 0.05   | 0.80 | sls  |       | tion is increased. |
| 10 | 30/70 | 0.11 | 0.02   | 0.30 | s    | 3.170 | Standard 30/70 polymer |
| 11 | 30/70 | 0.40 | 0.02   | 0.30 | s    | 3.184 |  |
| 12 | 30/70 | 0.11 | 0.034  | 0.30 | i    |       |  |
| 13 | 30/70 | 0.11 | 0.059  | 0.30 | i    |       |  |
| 14 | 30/70 | 0.11 | 0.02   | 0.09 | s    | 6.879 | reaction incomplete |
| 15 | 30/70 | 0.11 | 0.02   | 0.19 | s    | 3.451 |  |
| 16 | 35/65 | 0.11 | 0.02   | 0.30 | s    | 2.930 | standard 35/65 polymer |
| 17 | 35/65 | 0.11 | 0.027  | 0.30 | s    | 4.126 |  |
| 18 | 35/65 | 0.11 | 0.031  | 0.30 | i    |       |  |
| 19 | 35/65 | 0.11 | 0.036  | 0.30 | i    |       |  |
| 20 | 35/65 | 0.11 | 0.036  | 0.91 | i    |       |  |
| 21 | 35/65 | 0.11 | 0.088  | 0.91 | i    |       |  |
| 22 | 35/65 | 2.36 | 0.02   | 0.30 | s    | 2.843 | Type A polymer |
| 23 | 35/65 | 0.11 | 0.0295 | 0.30 | s    | 3.910 | very slow to dissolve |
| 24 | 35/65 | 0.11 | 0.0295 | 0.91 | s    | 1.658 |  |

It is further apparent that as the ratio of IPP to EGDMA decreases the molecular weight of the product increases.

Certain observations can be made at this point:

1. As the diester concentration is increased the material formed goes from a soluble polymer through a polymer that gels, to a highly cross-linked, insoluble product.

2. Samples containing a high concentration of IPP were found to turn opaque sooner than other samples. The reactions were observed to reach completion in a shorter length of time with the higher concentrations of initiator.

3. Based on the work to date, an excess of IPP can be used to produce a soluble polymer from a monomer containing as high as 0.035% diester although the product is likely highly branched.

4. Starting with monomer containing less than 0.03% EGDMA the IPP concentration can be used to control the molecular weight of the product. Below 0.03% diester level the polymers are soluble. Preferably the TABLE No. 6

SOLUBILITY OF POLY(HEMA) PRODUCED IN THE PRESENCE OF WATER

| Solvent | Soluble |
|---|---|
| Acetone | No |
| Acetone$_{80}$/Water$_{20}$ | Yes |
| Benzene | No |
| Carbon Tetrachloride | No |
| Chloroform | No |
| o-Dichlorobenzene | No |
| Dimethylformamide | Yes |
| Dimethylsulfoxide | Yes |
| Ethanol | Yes |
| Ethanol$_{90}$/Water$_{10}$ | Yes |
| Methanol | Yes |
| Methyl Cellosolve | Yes |
| Pyridine | Yes |
| Tetrahydrofuran | No |
| Tetrahydrofuran$_{80}$/Water$_{20}$ | Yes |
| Water | No |

Cross-Linkability

The film cast in the presence of 0.2% ammonium dichromate based on the polymer was found to be insoluble in methanol while the untreated control remained soluble.

Post-Cure

The polymer that remained in the 65°C. water bath an additional 4 hours beyond its cure time was found to have remained uncross-linked, as verified by a methanol solubility test. It may then be concluded that the length of the cure does not grossly affect the properties of the polymer produced in aqueous solution.

COPOLYMERS

Of the three copolymers, only $H_{40}/\overline{EeA}_{48}/\overline{HpA}_{12}$ had to be discarded because addition of water resulted in a phase separation between $\overline{EeA}$ and the water soluble HEMA and HpA. As a result the polymerized product was heterogeneous.

Both $H_{90}/MAA_{10}$ and $H_{90/Q}1_{10}$ copolymers were formed with no problem. Both were alcohol soluble. $H_{90}/MAA_{10}$ is quite similar in appearance to previous 35/65 polymers; $H_{90}/Q1_{10}$ however was transparent, brown (the color probably due to the fact that the Sipomer Q1 used was not purified) and gelatinous. It was also found to be soluble in water. It could be precipitated for purification in acid solution after which it could be redissolved in water giving a solution of pH 1.6. The methacrylic acid copolymer was not soluble in acid. However, when neutralized with NaOH it was found to be water soluble, giving a solution at a pH of about 7.0.

COMPARISON WITH SUSPENSION AND SOLUTION GRADE POLYMERS

The complete characterization of poly(HEMA) continued with a comparison of the properties of a 35/65 polymer with a sample of Polymer X and Polymer Y.

Viscosity

Each of the polymers was submitted for a reduced viscosity measurement. Included among the samples was a sample of suspension HEMA polymer which had been purified by reprecipitation from a 20% methanolic solution (Polymer Z). Table No. 7 contains the results which were reported by the Analytical Section.

TABLE No. 7

REDUCED VISCOSITY OF POLY(HEMA) PREPARED BY VARIOUS TECHNIQUES

| Sample | $n_{red}$(cp) |
|---|---|
| 35/65 | 2.93 |
| Polymer Z | 0.84 |
| Polymer X | 0.68 |
| Polymer Y | 1.13 |

An increase of 23.5 % in the viscosity of the suspension polymer upon a single purification is due to loss of low molecular weight species during this process and indicates that the suspension material contains a fairly broad range of molecular weights, although some of the loss may be due to entrapped monomer and/or toluene (the suspending agent).

According to the invention, purified poly(HEMA) having a 99.50% purity can be obtained with a single water wash which accompanies the grinding of the polymer, using a quantity of water equal to seven times the initial monomer weight.

Ultra pure poly(HEMA) with a minimum purity of 99.990% can be obtained by using an additional four leaches, each using seven times the initial monomer weight of fresh water.

Repeating the 35/65 (HEMA/water) experiment employing one pound of HEMA there was recovered 96.4% of material containing less than 0.3% unreacted monomer with the single water wash and grinding to 1–2 mm particles.

The product of the invention can be dried in the air and spread thin to avoid clumps, vacuum dried or dried in other conventional manner. The dried product can be micropulverized.

The presence of a small amount of methacrylic acid as an impurity does not adversely affect the solubility of the resulting polymer. While desirably the amount of MAA is not over about 0.15% it can be as much as 0.30% or even higher providing the amount of diester is kept low. The methacrylic acid can be eliminated completely.

Likewise any diethylene glycol monomethacrylate can be completely eliminated. It is normally present in not over 0.10%, usually not over 0.05%.

TABLE A

SAMPLE CALCULATION OF % CONVERSION
POLYMER (35/65) (HEMA/WATER)

| Extraction | | Volume of Liquid (ml) | Conc. of HEMA, % | Weight of HEMA (gms) |
|---|---|---|---|---|
| WASH | No. 1 | 270 | .1770 | 0.478 |
| | No. 2 | 270 | .0900 | 0.243 |
| LEACH | No. 1 | 265 | .0560 | 0.148 |
| | No. 2 | 260 | .0166 | 0.043 |
| | No. 3 | 255 | .0041 | 0.010 |
| | No. 4 | 250 | .0018 | 0.005 |

Total weight of monomer detected = 0.927 gms.
Initial Monomer Weight = 34.920

$$\% \text{ Untreated} = \frac{0.927}{34.920} \times 100 = 2.66\%$$

Monomer Conversion = 97.34%

What is claimed is:

1. A process for preparing a solid waterinsoluble, methanol-soluble hydrophilic polymer which consists essentially of polymerizing in water, monomers consisting essentially of (a) a monomer of the formula

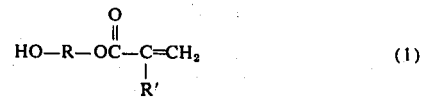

(1)

where R is an alkylene group of 2 to 3 carbon atoms, and wherein R' is hydrogen or methyl; with not more than 0.035 weight percent, based on the weight of said monomer of formula (1), of a diester of the formula

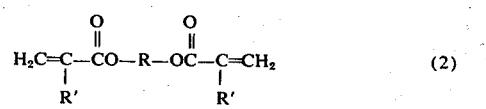

(2)

wherein R and R' have the above meanings or (b) said monomers of formula (1) and formula (2) together with a third monomer in an amount as high as 10%, said third monomer being methacrylic acid or

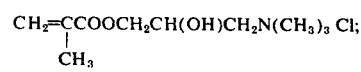

initiating polymerization by irradiation or a free radical initiator employing a ratio of total monomer to water from 10:90 to 70:30, conducting the polymerization for a period of time sufficient to produce said polymer, and recovering said polymer from the resulting reaction product mixture.

2. A process according to claim 1 wherein said monomers are (b), R is ethylene and R' is methyl.

3. A process according to claim 2 wherein there is present in the monomers 10% of methacrylic acid.

4. A process according to claim 2 where there is present in the monomers 10% of

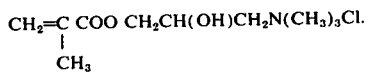

5. A process according to claim 1 wherein said monomers are (a).

6. A process according to claim 5 wherein the polymerization is initiated with isopropyl percarbonate.

7. A process according to claim 5 wherein a free radical initiator is included in the composition.

8. A process according to claim 7 wherein said monomer (1) is 2-hydroxyethyl methacrylate and wherein said diester (2) is ethylene glycol dimethacrylate.

9. A process according to claim 8 wherein the amount of diester is 0.02 to 0.035%.

10. A process according to claim 9 wherein the amount of diester is 0.02 to 0.03%.

11. A process according to claim 10 wherein the amount of diester is 0.02 to 0.025%.

12. A process according to claim 1 wherein the amount of diester is 0.02 to 0.035%.

13. A process according to claim 5 wherein said monomer (1) is 2-hydroxyethyl methacrylate and wherein said diester is ethylene glycol dimethacrylate.

14. A process according to claim 13, wherein a free radical initiator is included in the composition in an amount sufficient to produce a polymer having a molecular weight above about 250,000 by intrinsic viscosity in methoxyethane.

15. A process according to claim 13 including washing the polymer to a purity above 99.5%.

16. A process according to claim 13 wherein the ratio of 2-hydroxyethyl methacrylate to water is 35:65.

* * * * *